United States Patent
Kuballa et al.

(10) Patent No.: US 8,409,811 B2
(45) Date of Patent: Apr. 2, 2013

(54) LECTIN-BASED GLYCAN ASSAY

(75) Inventors: Jürgen Kuballa, Geesthacht (DE);
Kirstin Umnus, Geesthacht (DE);
Simone Cartellieri, Geesthacht (DE)

(73) Assignee: Galab Technologies GmbH, Geesthacht (DE)

( * ) Notice: Subject to any disclaimer, the term of this patent is extended or adjusted under 35 U.S.C. 154(b) by 86 days.

(21) Appl. No.: 12/677,693

(22) PCT Filed: Sep. 11, 2008

(86) PCT No.: PCT/EP2008/007838
§ 371 (c)(1),
(2), (4) Date: Mar. 11, 2010

(87) PCT Pub. No.: WO2009/033753
PCT Pub. Date: Mar. 19, 2009

(65) Prior Publication Data
US 2010/0216163 A1     Aug. 26, 2010

(30) Foreign Application Priority Data

Sep. 11, 2007 (EP) .................................. 07075800

(51) Int. Cl.
*G01N 33/53* (2006.01)
(52) U.S. Cl. ......................................... 435/7.1; 436/518
(58) Field of Classification Search .................... None
See application file for complete search history.

(56) References Cited

FOREIGN PATENT DOCUMENTS

| EP | 0 399 464 A2 | 11/1990 |
|---|---|---|
| EP | 0 662 611 A2 | 7/1995 |
| EP | 1 460 425 A | 9/2004 |
| WO | WO 89/04490 | 5/1989 |
| WO | WO 98/16825 | 4/1998 |
| WO | WO 03/087821 A | 10/2003 |
| WO | WO 2004/040307 | 5/2004 |

OTHER PUBLICATIONS

Lundy et al.: "An Antibody-Lectin Sandwich Assay for Quantifying Protein Glycoforms", in: Molecular Biotechnology, vol. 12, No. 2, 1999, pp. 203-206.
Anonymous: "Alkaline Phosphatase (*E coli* C75) from GE Healthcare, formerly Amersham Biosciences", retrieved from the internet on Nov. 6, 2008.

*Primary Examiner* — Jacob Cheu
(74) *Attorney, Agent, or Firm* — Henry M. Feiereisen, LLC (57) ABSTRACT

The invention relates to the use of deglycosylated detectors, especially secondary antibodies, for the determination of sugar structures of proteins, especially recombinant proteins. It further relates to the use of deglycosylated enzymes in the determination of sugar structures with the aid of an enzyme-substrate reaction; the invention further relates to a method of determining the sugar structures of proteins, a sugar determination kit and the use of said kit for the determination of sugar structures, especially of recombinant therapeutic proteins, preferably immunoglobulins.

13 Claims, 3 Drawing Sheets

Fig. 3

LECTIN-BASED GLYCAN ASSAY

CROSS-REFERENCES TO RELATED APPLICATIONS

This application is the U.S. National Stage of International application No. PCT/EP2008/007838, filed Sep. 11, 2008, which designated the United States and has been published as International Publication No. WO 2009/033753 and which claims the priority of European Patent Application, Ser. No. 07075800.8, filed Sep. 11, 2007, pursuant to 35 U.S.C 119 (a)-(d).

BACKGROUND OF THE INVENTION

The invention relates to the use of deglycosylated detectors, especially secondary antibodies, for the determination of sugar structures of proteins, especially recombinant proteins. It further relates to the use of deglycosylated enzymes in the determination of sugar structures with the aid of an enzyme-substrate reaction; the invention further relates to a method of determining the sugar structures of proteins, a sugar determination kit and the use of said kit for the determination of sugar structures, especially of recombinant therapeutic proteins, preferably immunoglobulins.

Recombinant therapeutic proteins are well-known in the prior art. For example, human proteins such as erythropoietin or antibodies have been recombinantly produced in CHO cells in the prior art. While this technology ensures reproduction of the protein amino acid sequence encoded in the DNA, the post-translational modifications of the recombinant protein, such as glycosylation, are variable depending on the cell clone and the culture conditions. When providing recombinant proteins, especially therapeutic proteins, it has to be kept in mind that, depending on the glycosylation, the sugar structures or protein glycosylation will give rise to a tissue-, cell-, development- and/or species-specific and typical behavior. Essential structural properties having central importance in therapeutic use are determined by the sugar structures of the proteins. For example, well-known recombinant therapeutic proteins are complete, i.e. intact, monoclonal antibodies.

To date, no method has been described in the prior art that would allow rapid and automatable determination of sugar structures, especially in recombinant therapeutic proteins such as intact monoclonal antibodies.

Up to now, complex procedures such as HPLC, MS or CE have been used in the prior art after removing the sugars. To this end it is necessary to remove the sugar structures from the protein using chemical or enzymatic hydrolysis. Although enzymatic procedures allow selective removal of specific structures, they are complex in practice and susceptible to interference. After removing the sugars, separation from the protein is necessary, which is frequently carried out using column chromatography. The steps of preparation and the sensitivity of subsequent analytic procedures, which frequently is low, result in the necessity of using more than a small amount of recombinant protein (500 to 1000 μg), which appears disadvantageous in practice. The determination of sugar structures often requires combining a number of analytic procedures, e.g. a mass-spectrometric investigation using MALDI-MS, which furnishes qualitative results and is not able to differentiate between hexoses, and a quantitative determination of defined sugars using HPLC or photometric methods. The use of the latter methods depends on the availability of pure glycans as comparative standards.

Inter alia, a method of detecting the terminal glycosylation pattern of IgG has been disclosed in the prior art. To this end, a sample comprising the protein to be investigated is immobilized on nitrocellulose. Thereafter, the proteins, preferably IgG, are treated in such a way that the sugar residues (Gal, GlcNAc) are liberated. The IgGs in the sample are detected using labeled lectins, said labeling in turn being effected by means of enzymes (WO 89/04490).

Another prior art method comprises immobilization of lectins on a plate and detection using a conjugate of secondary antibody and enzyme. In this method the lectin is selected in such a way that it can only recognize an abnormal sugar structure, for which reason it is not suitable for the determination of IgGs with galactose, fucose and other sugars (WO 98/16825).

Further, a method of detecting a glycoprotein using labeled lectins has been described in the prior art, wherein a so-called capture antibody (Fab portion) is immobilized first. The Fc portion thereof is removed so as to discard sugars that might impede the measuring operation. Disadvantageously, this method (WO 03/087821) has failed to solve the problem of Fab glycosylation and, in addition, the glycosylation of the enzyme in the determination of the sugar structures has not been accounted for.

EP 0 399 464 A2 discloses five methods wherein specific sugar residues are determined using plastic particles. Due to possible sugar structures on the substances used, these methods have failed to furnish satisfactory results as is the case with the method according to EP 0 662 611 A2 wherein glycoconjugates in a sandwich structure with lectins are investigated by initially immobilizing a capture antibody present in chemically treated form so as to inactivate the sugar and avoid false background signals.

Further prior art is identified in Lundy et al., 1999, WO 2004/040307, EP 1 460 452 and WO 03/087831 wherein various assays for the detection of glycoproteins have been described. Disadvantageously, the latter do not allow good determination of sugar structures of proteins because the individual measured signal cannot be sufficiently distinguished from the background noise.

None of the prior art methods are suitable for reliable and effective determination of sugar structures, especially in recombinant proteins such as immunoglobulins, particularly IgG.

SUMMARY OF THE INVENTION

In the light of the prior art it was completely surprising that a deglycosylated detection system can be used for the determination of at least one sugar structure, preferably all sugar structures, of proteins, especially recombinant, preferably recombinant immobilized proteins, said detection system comprising a deglycosylated marker enzyme and a binding structure, the binding structures preferably including or comprising at least secondary antibodies, protein A and/or fragments thereof, and the preferably recombinant proteins being recognition molecules, preferably primary antibodies selected from the group comprising IgM, IgE, IgD, IgA, IgY and/or IgW, preferably IgG. Most surprisingly, the teaching according to the invention can be used for a reliable and effective determination of sugar structures of recombinant proteins such as immunoglobulins (primary antibodies). More specifically, it was surprising that very good results in determining sugar structures can be achieved when, in addition to the marker enzyme, the binding structures, such as secondary antibody or detection antibody, are present in deglycosylated form.

On the one hand, the detection system according to the invention comprises a deglycosylated enzyme or marker enzyme and deglycosylated binding structures, i.e. detectors, which can be e.g. protein A, secondary antibodies and/or fragments thereof. According to the invention, it is preferably primary antibodies that are to be investigated so that a person of average skill in the art will know which binding structures could be used to detect the preferably primary antibodies. Those skilled in the art will know that in particular secondary antibodies, but also e.g. protein A or protein G or fragments of secondary antibodies or fragments of protein A or protein G can be used for this purpose. The above-mentioned molecules for investigation (marker enzyme and binding structures) must be present in deglycosylated form.

Accordingly, when referring to the determination of sugar structures of, in particular, recombinant proteins, the invention involves the surprising teaching of using deglycosylated detectors and enzymes for labeling (marker enzymes) or a deglycosylated detection system for the determination of sugar structures, said detection system, in addition to the deglycosylated marker enzyme, preferably comprising secondary antibodies, protein A, protein G and/or fragments thereof as detector, and the recombinant proteins being recognition molecules preferably selected from the group of IgG, IgM, IgE, IgD, IgA, IgY and/or IgB antibodies, particularly IgG. In particular, surprisingly good results are achieved in the determination of sugar structures of IgG.

To implement the teaching according to the invention it is preferred that e.g. the recombinant proteins to be investigated are present in immobilized form. For example, such immobilization can be effected by means of lectins. Most surprisingly, the use of lectins for immobilizing particularly the recombinant proteins results in improved determination of the sugar structures. It is of course also possible to use fluorescence-labeled markers instead of deglycosylated enzymes that are used e.g. in connection with avidin-streptavidin-biotin detection reactions.

When using enzymes in an avidin-streptavidin-biotin detection system, e.g. the biotin, the streptavidin and e.g. the alkaline phosphatase (AP) are deglycosylated. In other preferred embodiments it is possible to use horseradish peroxidase, β-galactosidase or an urease in addition to the alkaline phosphatase.

Accordingly, in a preferred embodiment of the invention a lectin is initially placed on an ELISA plate, which lectin is used to recognize the glycostructure of the sample to be investigated. To detect the bound sample, e.g. a secondary antibody is used in the further assay composition. In the meaning of the invention this is the deglycosylated detector, i.e. only one specific binding molecule or specific binding structure which can be labeled with biotin/vitamin H in a preferred embodiment. The deglycosylated detector, e.g. the secondary antibody, or a part thereof binds to the sample in a specific manner. In particular, an enzyme is used to screen or detect the bound secondary antibody. The enzyme is bound to the secondary antibody via the streptavidin-biotin system. In principle, direct chemical binding of the enzyme to the secondary antibody is also possible. The enzyme is e.g. an alkaline phosphatase or a horseradish peroxidase, β-galactosidase or urease. The enzymes for labeling are likewise present in deglycosylated form. Accordingly, the deglycosylated detection system in the preferred embodiment as described comprises a deglycosylated detector, such as the secondary antibody, and a deglycosylated enzyme, such as the alkaline phosphatase. The system described further comprises biotin and streptavidin, said streptavidin preferably being free of glycans. The non-glycosylated alkaline phosphatase is commercially available and derived from *Escherichia coli* (either recombinant or non-recombinant). In practice, however, this deglycosylated enzyme does not have particularly good activity compared to other glycosylated enzymes which can be used for comparison. Experience shows that further treatment, such as coupling to streptavidin, results in a drop of the enzyme activity. The particularly preferred inventive provision of active enzymes, such as the alkaline phosphatase, will be explained in connection with another preferred embodiment of the invention.

The detailed technical characteristics of the teaching according to the invention are defined with sufficient clarity to a person of average skill in the art. From the ELISA technique it is well-known to those skilled in the art that recombinant proteins, preferably in the form of antibodies, can be detected very efficiently and reliably by means of detectors if these detectors react specifically with the preferred antibodies. The detectors can be lectins and, in particular, secondary antibodies or fragments thereof.

Detection methods for visualizing preferably primary antibodies are well-known to those skilled in the art. In particular secondary antibodies are used with advantage to detect the primary antibodies. It will be appreciated that a person skilled in the art may also use other specific detectors for the primary antibodies, such as protein A or G. In the meaning of the invention, protein A is a 40 to 60 kDa protein originally derived from the cell walls of *Staphylococcus aureus* bacteria. Protein A is used with advantage for binding immunoglobulins (primary antibodies). Proteins of various species of mammals are bound, especially IgG. Protein A binds to the Fc region of immunoglobulins via interaction with the heavy chain. More specifically, protein A binds to human IgG1 and IgG2 as well as IgG2a and IgG2b with high affinity, but also IgM, IgA and IgG and recombinant monoclonal antibodies of non-human expression systems are bound in a specific manner. If a person skilled in the art is confronted with the object of binding primary antibodies, he or she will know that detectors other than secondary antibodies, protein A and/or fragments thereof can be used, in which context detectors in the meaning of the invention are molecules specifically interacting with the primary antibodies. Accordingly, it may also be preferred that the detector in the meaning of the invention is protein G. Protein G reacts with Ig1, Ig2 and Ig4 of human IgG in a particularly specific manner; furthermore, protein G binds to Ig3 and other therapeutic proteins. Surprisingly, the sugar structures of preferably primary antibodies can be detected very efficiently with detectors if these detectors, i.e. the binding structures, are present in deglycosylated form. Advantageously, deglycosylation can be effected using glycosidases such as endo- and exoglycosidases. According to the prior art, a number of enzymes are available to a skilled person for this purpose. In the context with this invention, enzymes such as N-glycanases, O-glycanases, endoglycosidases H, F1, F2, F3, and sialidases, galactosidases, mannosidases and fucosidases show surprisingly good results. Advantageous methods of chemical deglycosylation are hydrazinolysis or mild acid hydrolysis to remove sialic acids.

In addition to the secondary antibodies or protein A and/or G used for detecting the primary antibodies/therapeutic or diagnostic proteins, it is also possible to use fragments thereof. Without any inventive effort, a person skilled in the art can use simple routine tests to find out whether a fragment of a secondary antibody or of protein A or G can be used effectively to determine sugar structures of recombinant proteins, preferably antibodies.

In a preferred fashion the sugar structures are determined using an enzyme-substrate reaction wherein—as mentioned above—both the enzyme and the detector are deglycosylated, the latter two structures cocharacterizing the detection system according to the invention. Enzyme-substrate reactions are well-known procedures for detecting antibodies. Enzyme-substrate reactions frequently form part of the indirect method of detecting a specific antibody (primary antibody). A well-known procedure of the enzyme-substrate reaction envisages coupling a secondary antibody to an enzyme which initiates a color reaction with a substrate/chromogen, which reaction can be detected using measuring instruments or by simple visual inspection. Enzymes used with advantage are horseradish peroxidase with the substrates ABTS, OPD or TMB, bovine alkaline phosphatase with the substrates PNPP, FDP, NBT, or the enzymes β-galactosidase and glucose oxidase with corresponding substrates. When using alkaline phosphatase, phosphate compounds are employed as substrates from which phosphate is removed by the alkaline phosphatase so that the liberated compound can react to form a colored final product. For example, new fuchsin furnishes a pink/red reaction product, naphthol HS-MX phosphate forms a red dye and 5-bromo-4-chloro-3-indoxyl phosphate in compounds with nitroblue tetrazolium chloride is reacted to form a violet to blue dye. p-Nitrophenyl phosphate (PNPP) is reacted to form a yellow dye that can be detected at 405 nm, and fluorescein diphosphate (FDP) is detected by means of fluorescence measurement after conversion into fluorescein.

In a particularly preferred embodiment of the invention, deglycosylation is effected by cleaving the sugars from the enzyme, removing glycosylated molecule portions and/or preparing the enzyme in a bacterial expression system. Deglycosylation of the binding structure or detector is effected by cleaving the sugars from the binding structure, removing glycosylated molecule portions and/or by recombinantly preparing at least a part of or the complete binding structure. The terms "detector" and "binding structure" can be used synonymously.

In a particularly preferred embodiment, deglycosylation of preferably the marker enzyme is effected by at least three endoglycosidases. The deglycosylation is preferably effected on immobilized enzymes or markers. The use of a solid phase is advantageous because subsequent purification of the enzymes, such as alkaline phosphatase, is not required, which in turn would influence the activity or involve a high input of time which can be avoided by immobilizing. Preferred enzymes are endoglycosidases, especially F1, F2 and F3 (endo-NI-acetylglucosaminidase F1 (F2, F3), or endo F1 (F2, F3)), preferably used successively in the order as indicated. They are preferably prepared from *Elizabethkingia meningosepticum* (*Chrysobacterium meningosepticum* or *Flavobacterium meningosepticum*) or recombinantly expressed in *E. coli*. Advantageously and surprisingly, coupling these enzymes to solid phases produces virtually no loss of activity and, surprisingly, complete deglycosylation is achieved at the same time.

The use of the preferred endoglycosidases F1, F2 and F3 is particularly advantageous when the enzymes, preferably separately, are chemically bound on a support material. The preferred support material for chemical coupling of the enzymes is based on a methacrylate. In a preferred fashion the enzymes are coupled separately to separate supports. Similarly, the support material thus prepared is preferably used in three separate vessels (e.g. cartridges). Thus, the deglycosylation is effected successively in this particularly preferred embodiment. It is of course also possible to combine the support material, e.g. a support material having F1 and F3 bound thereto. In this event, the support material with F2 would be placed in a second separate vessel. However, the advantageous embodiment is the use of the coupled enzymes on support material in three separate vessels.

In a preferred fashion the alkaline phosphatase is glycosylated on the three supports mentioned above, with qualification being effected in the described inventive glycan array and in the enzyme activity test. It is also possible to immobilize the three endoglycosidases on a single support. The alkaline phosphatase can be obtained from various organisms of origin, such as calf intestine, bovine serum, bovine (recombinantly from *Pichia pastoris*), *E. coli*, and a streptavidin-AP conjugate is used as reference, wherein the AP (bovine) is glycosylated. Alkaline phosphatase is an enzyme which can be used to very good effect in the range of the ELISA technique. Also, the above-mentioned enzymes such as horseradish peroxidase, β-galactosidase or urease can be used to good effect. The enzymes can be used in their native forms or as conjugates. Using routine tests, a person skilled in the art can easily determine which conjugate should be used in dependence on the respective ELISA. For example, the enzymes can be present bound to antibodies, fragments thereof, to avidin or streptavidin, or to lectins. Streptavidin is a deglycosylated avidin complement. Surprisingly, despite the absence of glycans, it shows barely any or no difference to avidin. Streptavidin is preferably obtained from *Streptomyces avidinii* bacteria. Surprisingly, deglycosylation of all molecules which, according to the invention, represent the detection system results in a surprisingly improved method. For especially good determination in the meaning of the invention it is not sufficient to remove only certain sugar groups on certain molecules of the detection system. With glycosylated detectors or binding structures, a signal would also be detected in those cases where the sample binds, but also in those cases where the sample does not bind, but the secondary antibody does, or in those cases where the sample does not bind, the secondary antibody does not bind, but the enzyme does, so that the measurement cannot reliably determine the origin of the signal. Thus, for example, a lectin array generates a mixed signal which provides no information as to which signal has actually been generated by the sample to be investigated.

The use of the invention of the deglycosylated detectors/binding structures, preferably secondary antibodies, and marker enzymes is particularly in a method for the determination of the sugar structures of recombinant proteins, especially immunoglobulins, which method comprises the following steps:
a) providing the recombinant protein to be investigated, especially a recombinant therapeutic glycoprotein, said protein being present in immobilized form, preferably by means of a deglycosylated lectin;
b) incubating with a labeled binding structure, preferably a secondary antibody or a protein A or fragment thereof, which is deglycosylated; and
c) determining the interaction between the protein and the binding structure.

In this method, especially immunoglobulins selected from the group of IgG, IgM, IgE, IgD, IgA, IgY and/or IgW can be investigated for their sugar structures. That is, the use of the invention of deglycosylated binding structures (detectors) and marker enzymes or enzymes provides efficient, reliable, rapid and automatable methods for the determination of the sugar structures of proteins, especially immunoglobulins.

The method preferably involves initial placing of an array of lectins on a microtiter plate, which lectins recognize sugar structures preferably on IgG. In the prior art, lectins have been known as proteins having one or more binding sites for sugar structures. Lectins are therefore used to detect or remove sugar structures. The lectins can be native lectins obtained from organisms selected among *Agaricus bisporus, Aleuria aurantia, Amaranthus caudatus, Anguilla anguilla, Arachis hypogaea, Artocarpus integrifolia, Griffonia (Bandeiraea) simplicifolia I, Bauhinia purpurea alba, Cicer arietinum, Codium fragile, Canavalia ensiformis, Datura stramonium, Dolichos biflorus, Erythrina coralldendron, Erythrina cristagalli, Euonymos europaeus, Galanthus nivalis, Glycine max, Helix aspersa, Helix pomatia, Hippeastrum hybrid, Lens culinaris, Limulus polyphemus, Lotus tetragonolobus, Lycopersicon esculentum, Maackia amurensis, Maclura pomifera, Narcissus pseudonarcissus, Phaseolus coccineus, Phaseolus limensis, Phaseolus vulgaris, Phytolacca americana, Pisum sativum, Phosphocarpus tetragonolobus, Ricinus communis, Sambucus nigra, Solanum tuberosum, Sophora japonica, Triticum vulgaris, Tritrichomonas mobilensis* (protozoa), *Ulex europaeus, Vicia fabs, Vicia villosa, Viscum album, Wisteria floribunda* and/or recombinant lectins. In one embodiment of the method, different lectins (at least one) are immobilized on the surface of a microtiter plate. The lectins are selected in such a way that they recognize sugar structures preferably on IgG, particularly N-acetylglucosamine, galactose, mannose, fucose and sialic acid (N-acetylneuraminic acid). When a specific sugar structure is recognized on IgG, the IgG molecule will be retained on the surface, while other molecules not including this structure will be washed off.

Protein A or fragments thereof can be used as preferred control for the IgGs. Protein A binds to a non-glycosylated portion of IgG (Fc), thus providing a reference signal which is proportional to the total amount of IgG employed in the method. The protein A signal can therefore be used for controlling the process and for calibration so as to obtain quantitative information from the process. The individual results for the sugar structures can be compared to the protein A control and related to the IgG overall content.

After providing the array of lectins on a microtiter plate in the preferred embodiment, this array can be contacted with the sample comprising the glycoproteins to be investigated. More specifically, the glycoproteins to be investigated are recombinant antibodies referred to as primary antibodies. Primary antibodies are those molecules wherein the sugar structure is determined by detecting them preferably with a second antibody (=secondary antibody). Advantageously, the sample can be employed without further preparation, such as labeling the glycoproteins included therein. The prior art requires complex sample preparation.

The above process step provides an array of lectins on a microtiter plate, in which array the specifically binding glycoproteins to be investigated are present in bound form.

The interaction between the protein to be investigated and the lectin can be determined using an enzyme-substrate reaction familiar to those skilled in the art, particularly such as known to the skilled artisan from ELISA tests. According to the invention, the term "enzyme", e.g. in connection with an enzyme-substrate reaction, may refer to the marker enzyme, i.e. the enzyme being used for detection. The structures used to deglycosylate said marker enzyme, or enzyme, are also enzymes in biochemical terms, e.g. endoglycosidases, preferably F1, F2 and F3, which, placed separately on supports, can be used successively in the order as mentioned to deglycosylate the marker enzyme or detector. From the overall disclosure, a person skilled in the art will recognize in which cases the term "enzyme" refers to a molecule for detection (marker enzyme) and in which cases a molecule for deglycosylation is used.

Figure 1:
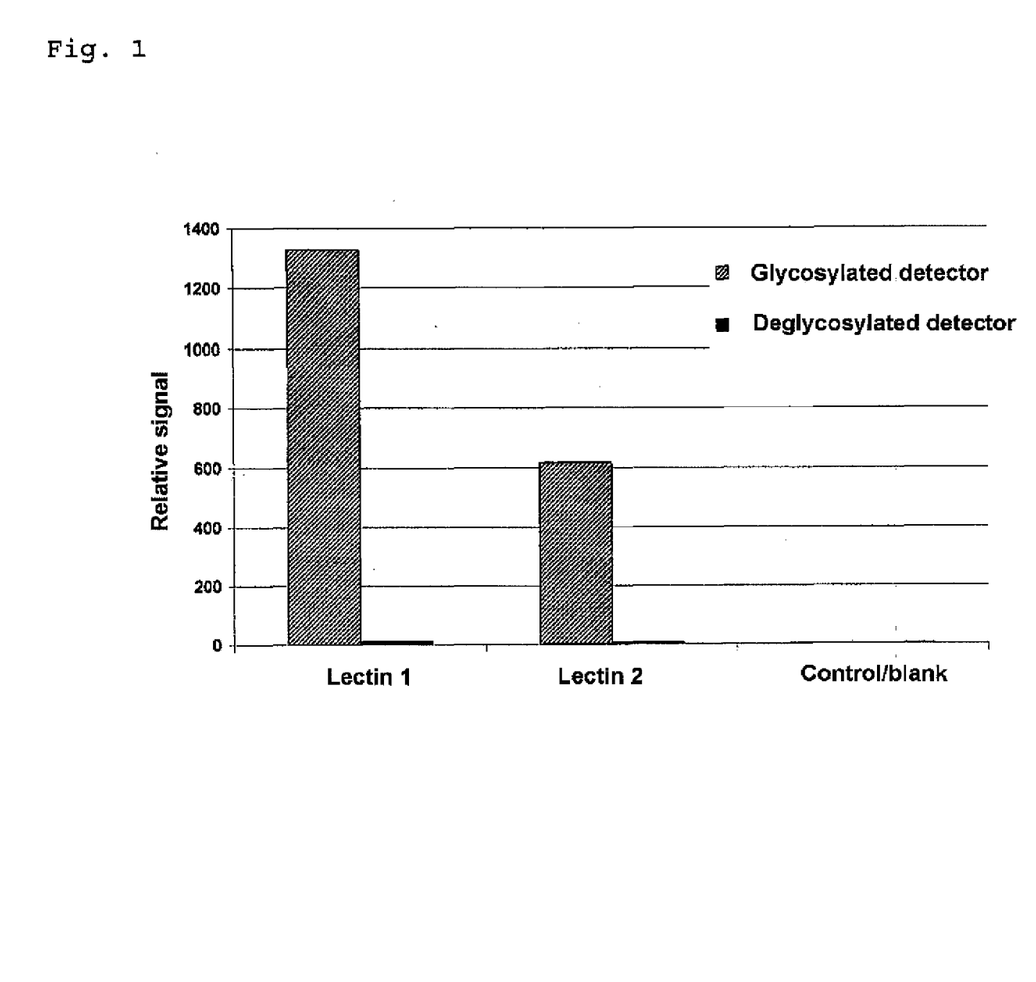
FIG. 1 shows signals of the glycosylated secondary antibody and control.

In the meaning of the invention the interaction with a so-called detector or binding structure is determined in such a way that the detector/binding structure specifically recognizes in the sample the glycoprotein to be investigated, and especially preferably at a position which is not the glycan. In particular, the detector or detector molecule or the binding agent or binding structure is a secondary antibody or a fragment thereof, but it may also be a protein A or a fragment thereof. Accordingly, the terms detector or binding structure or binding agent or detection molecule or detector molecule can be used synonymously in the meaning of the invention. A person of average skill in the art will recognize that the detector according to the invention, present in deglycosylated form, is preferably a secondary antibody or a part thereof or protein A or G or a fragment thereof and is an essential component of the deglycosylated detection system according to the invention. If the deglycosylated marker enzyme is present in addition to the deglycosylated detector or the deglycosylated binding structure and the deglycosylated detector has e.g. biotin and the deglycosylated marker enzyme has e.g. streptavidin, this combination as mentioned represents the preferred detection system according to the invention, which is a deglycosylated detection system.

it is essential to the invention that the detector molecules are present in deglycosylated form so as to exclude false-positive background signals. As demonstrated in experiments, the use of glycosylated detectors furnishes a mixed result determined by both the sugar structures of the detector and those of the protein to be analyzed. Application Example 1 shows the signals of a glycosylated detector on 2 different lectins.

Figure 2:
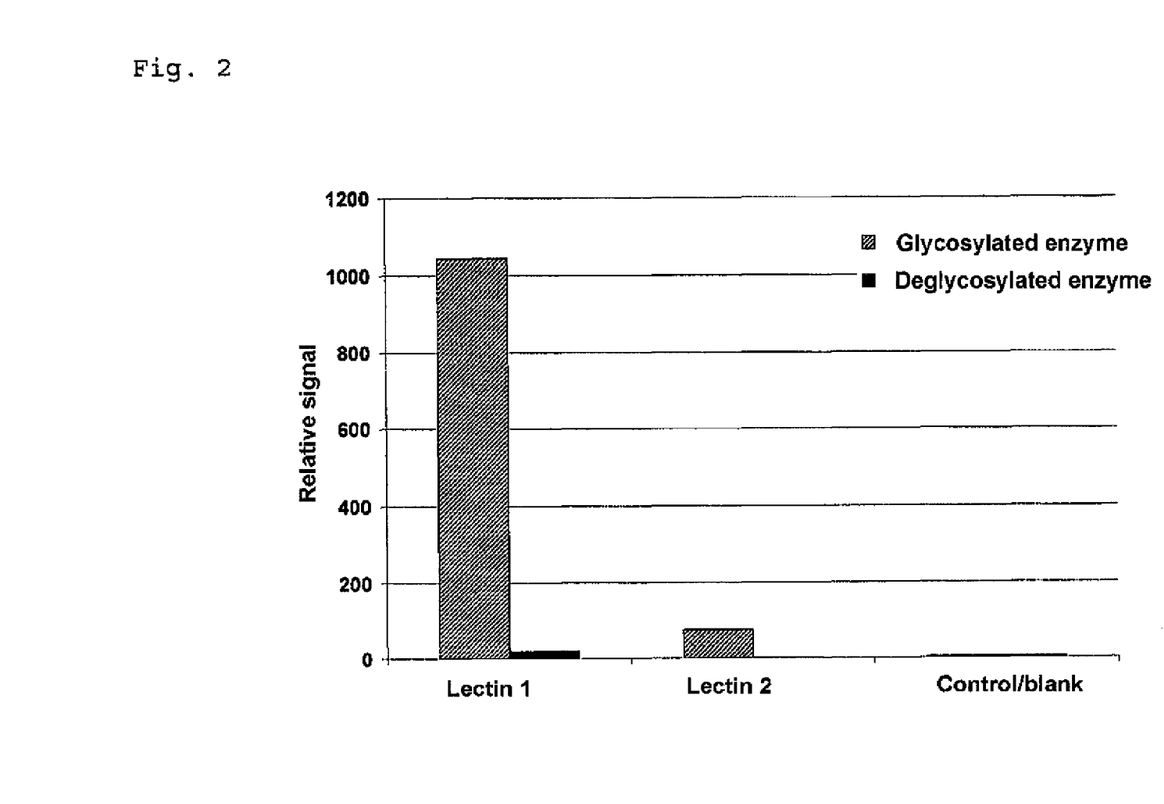
FIG. 2 shows a signal of the glycosylated enzyme on the lectin and control.

Surprisingly, additional deglycosylation of the enzyme used in the enzyme-substrate reaction, i.e. the marker enzyme, results in surprisingly good exclusion of false-positive background signals so that easy, reliable and efficient determination of the sugar structures of recombinant therapeutic proteins is possible. In particular, proteins regarded as therapeutics, such as antibodies, can be determined in a particularly reliable and efficient manner with the method according to the invention. As demonstrated in experiments, the use of glycosylated enzymes, i.e. marker enzymes, furnishes a mixed result determined by both the sugar structures of the enzyme and those of the protein to be analyzed. Application Example 2 shows a comparison of a glycosylated and a non-glycosylated enzyme on a lectin-coated microtiter plate.

In a preferred embodiment of the invention the interaction between the protein and the detector is determined via an enzyme-substrate reaction.

In another particularly preferred embodiment of the invention the recombinant protein is present in immobilized form. Immobilization in the meaning of the invention involves various methods of fixing the recombinant proteins, especially antibodies, particularly IgG. Fixing of antibodies, in particular, can be achieved by exposure to biological, chemical or physical action. For example, the recombinant proteins/antibodies can be fixed by binding to a support, but also by crosslinking, inclusion, or by incorporating in microcapsules. In the event of binding to a support (e.g. microtiter plate), fixing is effected by adsorption, ionic binding or covalent binding. For example, the recombinant proteins/antibodies can also be fixed on the surface by means of an immobilized secondary antibody (capture antibody) or protein A. In a preferred manner, fixing will not adversely modify the protein in its sugar structure. In the event of inclusion in a semipermeable membrane, fixing takes place in the form of inclusion in gels, microcapsules or fibers.

In a preferred fashion the recombinant protein, especially the antibody, preferably IgG, is fixed on a microtiter plate. Microtiter plates are preferably plastic plates usually made of polystyrenes or polyvinyl chloride which can be used for various immunological operations. Common microtiter plates have 96 wells each having a capacity of 250 µl. Of course, it is also possible to use microtiter plates made of other materials or to vary the number of wells. For example, microtiter plates having 384 or 1536 wells are advantageous in high-throughput.

In a particularly preferred embodiment of the invention the recombinant protein, especially the antibody, preferably IgG, is fixed/immobilized via a lectin. More specifically, lectins in the meaning of the invention are complex proteins which bind the specific carbohydrate structures of the protein to be investigated, thereby being able to fix the latter. In particular, lectins are obtained from some types of plants, especially from leguminous plants, but also from animal organisms and cells. Preferred lectins have specificity for galactose, mannose, acetylglucosamine, fucose and sialic acids (N-acetylneuraminic acid) and are obtained from e.g. jack bean, garden bean, *ricinus* bean, soybean, lentil, pea, peanut, wheat, potato, snowdrop, elderberry, Chinese yellow wood, gorse, spindletree and/or from fungi such as orange peel fungus.

In a particularly preferred embodiment the therapeutic recombinant glycoprotein to be investigated, especially the primary antibody, is immobilized in such a way that it is fixed via a lectin which is present immobilized on a microtiter plate. Combinations of microtiter plate and lectin immobilized thereon are known to those skilled in the art from other uses. For example, such combinations are known from enzyme immunoassays. Enzyme immunoassays comprise enzymes and substrates and/or radioisotopes. All these terms are common terms in the prior art and can be found in encyclopedias so that detailed explanations are not required; the same applies to the terms detector, binding structures, marker enzyme or detection system. Immobilization of a lectin on a microtiter plate is a preferred element of the well-known solid-phase technology, e.g. affinity chromatography.

In a preferred fashion, lectins specifically interacting with a sugar structure of the recombinant protein, especially antibodies, preferably IgG, are immobilized on the microtiter plate. Specific interaction is an interaction that allows conclusions as to the sugar structure of a recombinant protein. An interaction proceeding in such a way that the sugar structure cannot be determined is not specific in the meaning of the invention. For example, non-specific interaction would be interaction of an agent with the microtiter plate, with the lectin and/or the recombinant protein, especially the sugar structure thereof, so that determination of the sugar structure is not possible. This design of the method furnishes especially good results.

In advantageous embodiments of the invention it is particularly preferred to use the recombinant protein/glycoprotein without a label so that, advantageously, preparation of the sample comprising the glycoprotein/recombinant protein to be investigated, preferably the antibody, especially IgG, e.g. by labeling with enzymes, biotin/streptavidin, fluorescent dyes such as FITC or isotopes is not required. Of course, as indicated above, labeling of the marker enzymes with relatively special additional enzymes or with fluorescent dyes or isotopes is possible.

In a particularly preferred embodiment the method according to the invention comprises the following steps:
 a) binding at least one lectin on a microtiter plate;
 b) contacting the lectin with the recombinant protein/glycoprotein to be investigated;
 c) incubating with a labeled detector/binding structure comprising a secondary antibody, protein A and/or fragments thereof;
 d) detecting the detector/binding structure by means of an enzyme-substrate reaction, said detector/binding structure and said enzyme being in deglycosylated form.

In this case, a person skilled in the art will recognize that "enzyme" is understood to be the marker enzyme which is present in deglycosylated form, preferably together with streptavidin which is free of glycans. Surprisingly, the method allows highly efficient determination of the sugar structures.

Of course, it is also possible to modify the method of the invention as follows so that it comprises the following chronological sequence of steps:
 a) binding at least one deglycosylated detector, preferably a secondary antibody, on a microtiter plate;
 b) contacting the detector with the protein/glycoprotein to be investigated;
 c) incubating with a labeled lectin;
 d) detecting the detector by means of an enzyme-substrate reaction, said detector and said enzyme being in deglycosylated form.

In the above preferred method as well, a person skilled in the art will recognize that "enzyme" is understood to be the marker enzyme and "detector" is understood to be the binding structure of the invention because "binding structure" and "detector" can be used synonymously in the meaning of the invention. Both of the above cases preferably refer to a deglycosylated molecule such as a secondary antibody, protein A or G or a fragment thereof.

Complete deglycosylation is particularly preferred in connection with the use of the invention of the deglycosylated detector or enzyme or fragment. Complete deglycosylation of the detector or a fragment thereof is achieved e.g. by enzymatic cleavage of the detector. If the detector is a secondary antibody, the non-glycosylated Fab fragment or Fab-2 fragment is subsequently used. Non-glycosylated Fab fragments are obtained either by selection among native, polyclonal forms or by recombinant, monoclonal production of a secondary antibody or Fab fragment after switching off potential glycosylation sites on the Fab portion. These methods are well-known to those skilled in the art. Preferred enzymes for enzymatic cleavage of the detector, especially the secondary antibody, are papain and pepsin. Furthermore, it is advantageous to perform complete or partial deglycosylation of the detector by treating the latter with sugar-removing enzymes, preferably glycosidases. The following enzymes can preferably be used for this purpose: endo F1, endo F2, endo F3, PNGase F, N-glycanase, galactosidase, mannosidase, sialidase and/or fucosidase. In this way it is possible to treat, i.e. deglycosylate, the complete detector/secondary antibody or fragments thereof (Fc, Fab, Fab-2). Another preferred variant of deglycosylation is chemical treatment using e.g. periodate. It can also be advantageous to use a secondary antibody from expression systems which only synthesize defined sugar structures, such as high-mannose type, in yeast cells or selected, modified eukaryotic systems. Another preferred variant is the use of a detector (e.g. protein A) from expression systems lacking the capability of post-translational modification, such as prokaryotic systems.

Providing the deglycosylated enzyme is preferably possible by producing the latter recombinantly or natively in prokaryotic expression systems so that it is in non-glycosylated form. In a particularly preferred fashion this can be done by using e.g. native alkaline phosphatase or recombinant alkaline phosphatase from *E. coli*. In addition, the preferred complete enzymatic deglycosylation of the enzyme can be effected with the following enzymes: endo F1, endo F2, endo F3 (also described as endo H F1, endo H F2, endo H F3), glycanase, galactosidase, mannosidase, sialidase and/or fucosidase. Furthermore, it is possible to use an enzyme from expression systems which only synthesize defined sugar structures (e.g. high-mannose type, in yeast cells or other selected eukaryotic systems).

In another preferred embodiment of the invention the recombinant protein is immobilized via a lectin.

In another preferred embodiment of the invention the lectin is present immobilized on a microtiter plate.

In another preferred embodiment of the invention the lectins are selected so as to specifically interact with a sugar structure of the recombinant protein.

The teaching of the invention provides a method for particularly efficient and interference-free determination of sugar structures of recombinant proteins. In particular, it was completely surprising that especially immobilized, recombinant proteins can be investigated for their sugar structures to good effect by means of a deglycosylated detection system if said deglycosylated detection system comprises a deglycosylated marker enzyme, preferably for implementing an enzyme-substrate reaction, and a deglycosylated binding structure, preferably a secondary antibody. Such a method has neither been known in the prior art nor made obvious therein. Lundy et al., Molecular Biotechnology, Vol. 12, No. 2, pp. 203-206, September 1999, claim that the assay presented therein could be adapted to any type of problem. In this document the antibody is deglycosylated, which is said to allow adaptation to any further assays for the determination of glycoproteins. In the light of this document a person skilled in the art would therefore have no motivation to provide a deglycosylated detection system such as the system according to the invention because the cited document teaches the artisan that by deglycosylating the antibodies the background noise can be reduced to such a value that optimum determination of glycoproteins is possible. However, tests conducted by the inventors reveal that the background noise cannot be avoided optimally and good sensitivity cannot be ensured either, especially since the problems as to sensitivity of detection has not been discussed in the disclosure mentioned above. Moreover, the described removal of glycans via PNGase F is not sufficient to provide an assay having sufficient sensitivity. According to the disclosure mentioned above, the ALP (AP) enzyme is present in glycosylated form so that the method described therein cannot be used for different target structures. In particular, investigating recombinant proteins such as antibodies requires especially fine adjustment and proper selection of the assay components. Antibodies frequently have less glycosylation on the Fc portion, and the glycans are not optimally accessible to the lectin in steric terms. Therefore, the method described in the disclosure mentioned above cannot be used in the investigation of antibodies because an especially high level of sensitivity is required therein. It is only the method according to the invention that achieves the required sensitivity. To a person skilled in the art, the overall disclosure of the above-mentioned document is not a motivation to combine the latter with e.g. EP 1 460 425. In a preferred fashion, complete absence of glycostructures on the marker enzyme is only achieved by deglycosylation on a support. The preferred combination of the glycosidases F1, F2 and F3 results in a sufficiently sensitive assay. Deglycosylation is preferably performed prior to conjugation to e.g. streptavidin. This preferred embodiment ensures both absence of glycostructures in the detection system according to the invention and sufficient activity after conjugation. Preferred is chemical conjugation of streptavidin to the enzyme.

Without intending to be limiting, the invention will be explained in more detail below with reference to the examples (Application Examples 1 to 3).

DETAILED DESCRIPTION OF PREFERRED EMBODIMENTS

APPLICATION EXAMPLE 1(FIG. 1)

The surface of a microtiter plate was coated with concanavalin A (1) and *Sambucus nigra* agglutinin (2) lectins. To determine which signal came from a glycosylated detector, a native secondary antibody (from goat) was measured directly without addition of sample. A deglycosylated detector (protein A) was measured for comparison.

The results show high signals of the glycosylated secondary antibody (detector) on both lectins used. As expected, the control surface (blank=serum albumin) shows no binding of glycosylated detector. Likewise, the deglycosylated protein A detector gives no signals on the lectins.

The application example shows that false-positive background signals can be excluded only when using a deglycosylated detector.

APPLICATION EXAMPLE 2(FIG. 2)

The surface of a microtiter plate was coated with *Aleuria aurantia* (1) and *Galanthus nivalis* agglutinin (2) lectins, protein A and serum albumin (blank). To determine which signal came from a glycosylated enzyme, a glycosylated enzyme and a deglycosylated enzyme (here: alkaline phosphatase) were measured for comparison. For elucidation, no sample, e.g. therapeutic IgG, was added in this case.

The results show a high signal of the glycosylated enzyme on the lectin, whereas the deglycosylated enzyme shows no signal. As expected, the protein A and serum albumin control surfaces show no binding of glycosylated enzyme and deglycosylated enzyme.

The application example shows that false-positive background signals can be excluded only when using a deglycosylated enzyme.

Figure 3:
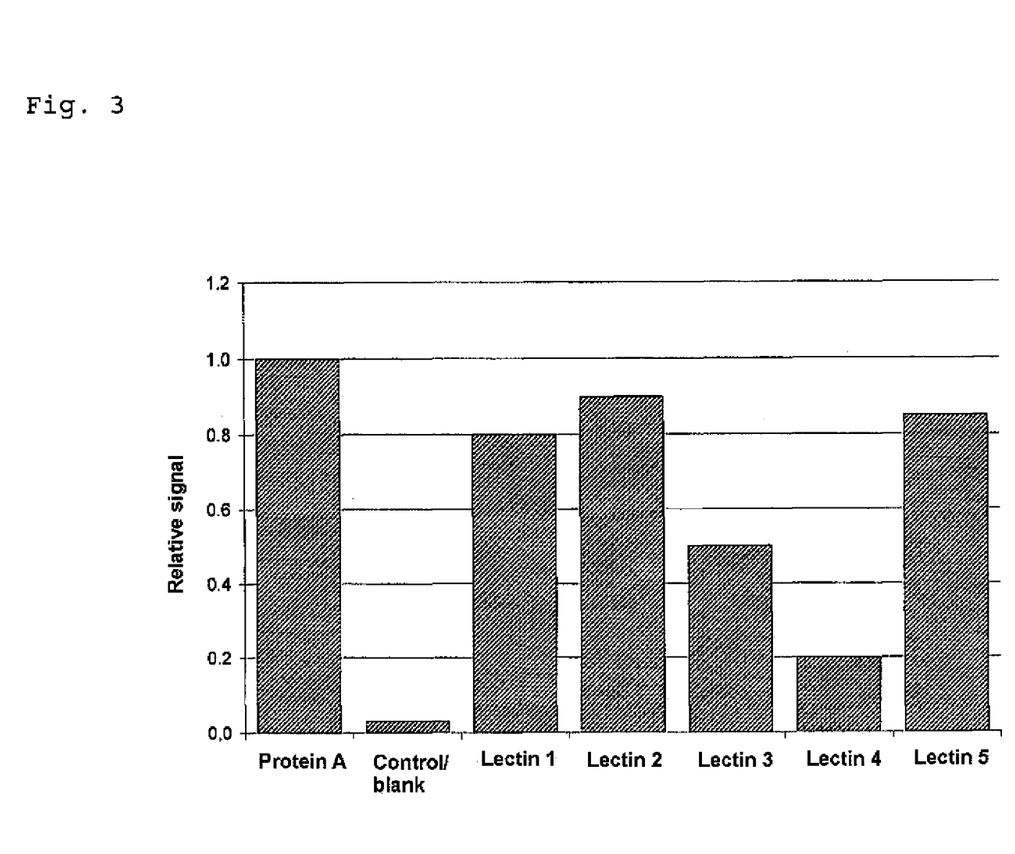
FIG. 3 shows signals for the different lectins.

APPLICATION EXAMPLE 3(FIG. 3)

The surface of a microtiter plate was coated with an array of lectins (1-5), protein A as control and serum albumin (blank). The sample under investigation, a recombinant, therapeutic IgG, was subsequently placed thereon to bind to the lectins in accordance with the sugar structures present. For detection, a biotinylated detector (deglycosylated Fab fragment of a secondary antibody) was used which, following a wash step, was screened by means of streptavidin-alkaline phosphatase (deglycosylated, recombinantly from *E. coli*) and p-nitrophenyl phosphate substrate.

The results show signals of different height for the different lectins, which can be attributed to the particular sugar structures of the sample. The protein A signal is used for standardization to allow direct comparison of different samples. As demonstrated in the application example, the assay according to the invention is suitable for rapid, automatable and interference-free analysis of the sugar structures of recombinant proteins.

What is claimed is:

1. A method for the determination of the sugar structures of recombinant proteins, wherein the method comprises the following steps:
 a) providing a recombinant protein to be investigated, which is a recombinant therapeutic glycoprotein, said protein being present in immobilized form, through a deglycosylated Pectin, wherein the lectin is present immobilized on a support;
 b) incubating said recombinant protein with a labelled binding structure including at least one of, a secondary antibody or a protein A or fragment thereof, which is deglycosylated; and
 c) determining the binding between said recombinant protein and the binding structure wherein the sugar structure of said recombinant protein can be derived from said lectin.

2. The method as claimed in claim 1, wherein the determination of the binding between said recombinant protein and the binding structure is performed using a marker enzyme-substrate reaction, said enzyme being deglycosylated and selected from the group comprising at least one of alkaline phosphatase, horseradish peroxidase, β-galactosidase and urease.

3. The method as claimed in claim 2, wherein deglycosylation is effected by, cleaving the sugars from the enzyme, and at least one of removing glycosylated molecule portions and preparing the enzyme in a bacterial expression system.

4. The method as claimed in claim 1, wherein the interaction between the protein and the binding structure is determined via an enzyme-substrate reaction.

5. The method as claimed in claim 1, wherein the recombinant proteins are used without a label.

6. The method as claimed in claim 1, wherein the method comprises the following steps:
 a) binding at least one lectin on a microtiter plate;
 b) contacting the lectin with the recombinant protein/glycoprotein to be investigated;
 c) incubating with a labelled binding structure comprising at least one secondary antibody, protein A and/or a marker enzyme and/or fragments thereof;
 d) detecting the labelled binding structure by means of a marker enzyme-substrate reaction, said secondary antibody, said protein A and/or fragments thereof and said enzyme being in deglycosylated form.

7. The method as claimed in claim 1, wherein deglycosylation of the binding structures is effected by at least one of, cleaving the sugars from the binding structure, removing glycosylated molecule portions and by recombinantly preparing at least part of the deglycosylated binding structures.

8. The method as claimed in claim 1, wherein deglycosylation of the marker enzyme is effected by at least three endoglycosidases.

9. The method as claimed in claim 8, wherein the at least three endoglycosidases are F1, F2 and F3.

10. The method use as claimed in claim 1, wherein an endoglycosidase is coupled to a solid phase for deglycosylation.

11. The method of claim 1, wherein the support is a microtiter plate.

12. A method for the determination of the sugar structures of immunoglobulins, wherein the method comprises the following steps:
 a) providing the immunoglobulin to be investigated, said immunoglobulin being present in immobilized form, through a deglycosylated lectin, wherein the lectin is present immobilized on a microtiter plate,
 b) incubating said immunoglobulin with a labeled binding structure including at least one of, a secondary antibody or a protein A or fragment thereof, which is deglycosylated; and
 c) determining the binding between the immunoglobulin and the binding structure wherein the sugar structure of said recombinant protein can be derived from said lectin.

13. A method for the determination of the sugar structures of recombinant proteins, wherein the method comprises the following steps:
 a) providing the recombinant protein to be investigated, which is a recombinant therapeutic glycoprotein, said protein being present in immobilized form, through a deglycosylated lectin, wherein the lectin is present immobilized on a microtiter plate; said immobilization of said recombinant protein by means of lectin occurs when said recombinant protein comprises a sugar structure that is recognized and bound by said lectin;
 b) incubating said recombinant protein with a labelled binding structure including at least one of, a secondary antibody or a protein A or fragment thereof, which is deglycosylated; and
 c) determining the binding between the said recombinant protein and the binding structure wherein the sugar structure of said recombinant protein can be derived from said lectin.

* * * * *